(12) United States Patent
Rose et al.

(10) Patent No.: US 8,492,762 B2
(45) Date of Patent: Jul. 23, 2013

(54) ELECTRICAL INTERFACE FOR A SENSOR ARRAY

(75) Inventors: James Wilson Rose, Guilderland, NY (US); Kevin Matthew Durocher, Waterford, NY (US); Donna Marie Sherman, East Greenbush, NY (US); Oliver Richard Astley, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 1384 days.

(21) Appl. No.: 11/426,617

(22) Filed: Jun. 27, 2006

(65) Prior Publication Data

US 2008/0006773 A1 Jan. 10, 2008

(51) Int. Cl.
*H01L 23/58* (2006.01)

(52) U.S. Cl.
USPC ............. 257/48; 257/691; 257/416; 257/422; 257/433; 257/435; 257/443; 257/659

(58) Field of Classification Search
None
See application file for complete search history.

(56) References Cited

U.S. PATENT DOCUMENTS

| | | | | |
|---|---|---|---|---|
| 3,622,432 A | * | 11/1971 | McCluer et al. | 428/215 |
| 4,599,680 A | * | 7/1986 | Gibson et al. | 361/684 |
| 4,766,518 A | * | 8/1988 | Pedelaborde-Augas et al. | 361/714 |
| 4,833,334 A | * | 5/1989 | Valy et al. | 250/515.1 |
| 4,969,167 A | | 11/1990 | Zupancic | |
| 5,248,885 A | | 9/1993 | Sato et al. | |
| 5,355,102 A | | 10/1994 | Kornrumpf et al. | |
| 5,444,752 A | | 8/1995 | Dobbs et al. | |
| 5,527,741 A | | 6/1996 | Cole et al. | |
| 5,635,754 A | * | 6/1997 | Strobel et al. | 257/659 |
| 5,819,137 A | | 10/1998 | Hoffman et al. | |
| 5,825,042 A | * | 10/1998 | Strobel et al. | 250/515.1 |
| 6,261,508 B1 | * | 7/2001 | Featherby et al. | 264/408 |
| 6,262,362 B1 | * | 7/2001 | Czjakowski et al. | 174/360 |
| 6,455,864 B1 | * | 9/2002 | Featherby et al. | 250/515.1 |
| 6,465,790 B1 | | 10/2002 | Monnet et al. | |
| 6,510,195 B1 | * | 1/2003 | Chappo et al. | 378/19 |
| 6,594,156 B1 | * | 7/2003 | Van Antwerp et al. | 361/816 |
| 6,605,818 B1 | * | 8/2003 | Cornog et al. | 250/518.1 |
| 6,613,978 B2 | * | 9/2003 | Czjakowski et al. | 174/388 |
| 6,720,493 B1 | * | 4/2004 | Strobel et al. | 174/388 |

(Continued)

FOREIGN PATENT DOCUMENTS

EP 0657938 6/2005

OTHER PUBLICATIONS

Office Action dated Nov. 14, 2008 U.S. Appl. No. 11/532,567.
Office Action dated Feb. 25, 2009 U.S. Appl. No. 11/532,567.

(Continued)

*Primary Examiner* — David E Graybill
(74) *Attorney, Agent, or Firm* — Jason K. Klindtworth

(57) ABSTRACT

An interface circuit for a sensor array is provided. The interface circuit may be made up of an integrated circuit package that provides a first region and a second region. The first region may be spaced apart and opposite to the second region of the package. The first region of the package may provide a plurality of interfaces for interconnecting to an integrated circuit in the package a plurality of signals from the sensor array and having a first electrical characteristic, such as analog and test signals. The second region of the package may provide a plurality of interfaces for interconnecting to the integrated circuit a plurality of signals having at least one electrical characteristic different than the first characteristic, such as power and operational digital signals.

16 Claims, 3 Drawing Sheets

U.S. PATENT DOCUMENTS

| | | | |
|---|---|---|---|
| 6,858,795 B2* | 2/2005 | Czjakowski et al. | 174/350 |
| 6,900,565 B2 | 5/2005 | Preston | |
| 6,909,775 B2 | 6/2005 | Ray et al. | |
| 6,933,813 B2 | 8/2005 | Burdick, Jr. et al. | |
| 6,987,833 B2* | 1/2006 | Du et al. | 378/98.9 |
| 6,990,176 B2* | 1/2006 | Sherman et al. | 378/98.8 |
| 6,999,550 B2* | 2/2006 | Tang | 378/15 |
| 7,065,173 B2* | 6/2006 | Lacey et al. | 378/19 |
| 7,163,752 B2* | 1/2007 | Coker et al. | 428/615 |
| 7,215,734 B2* | 5/2007 | Hsieh et al. | 378/19 |
| 7,236,562 B2* | 6/2007 | Joshi et al. | 378/19 |
| 7,247,856 B2 | 7/2007 | Hoge | |
| 7,249,886 B1* | 7/2007 | Chao et al. | 378/207 |
| 7,251,306 B2* | 7/2007 | Sauer et al. | 378/4 |
| 7,285,837 B2 | 10/2007 | Huang et al. | |
| 7,329,875 B2 | 2/2008 | McEvoy | |
| 7,348,564 B2* | 3/2008 | Wollenweber et al. | 250/363.04 |
| 7,408,258 B2 | 8/2008 | Salmon | |
| 2002/0011097 A1 | 1/2002 | Kuderer et al. | |
| 2003/0072478 A1* | 4/2003 | Claus et al. | 382/131 |
| 2003/0155516 A1 | 8/2003 | Spartiotis et al. | |
| 2004/0022351 A1 | 2/2004 | Lacey et al. | |
| 2004/0071259 A1 | 4/2004 | Lacey et al. | |
| 2004/0099947 A1 | 5/2004 | Burdick, Jr. et al. | |
| 2004/0159713 A1 | 8/2004 | Schmidt et al. | |
| 2004/0202287 A1 | 10/2004 | Mueller | |
| 2004/0228450 A1 | 11/2004 | Mueller | |
| 2004/0240625 A1 | 12/2004 | Kendall | |
| 2005/0045358 A1 | 3/2005 | Arnold | |
| 2005/0084069 A1* | 4/2005 | Du et al. | 378/98.9 |
| 2005/0094763 A1* | 5/2005 | Sherman et al. | 378/19 |
| 2005/0117698 A1* | 6/2005 | Lacey et al. | 378/19 |
| 2005/0175142 A1* | 8/2005 | Tang | 378/15 |
| 2006/0002507 A1* | 1/2006 | Hsieh et al. | 378/19 |
| 2006/0104410 A1* | 5/2006 | Sauer et al. | 378/4 |
| 2006/0109956 A1 | 5/2006 | Lacey | |
| 2006/0153277 A1 | 7/2006 | Yoshida | |
| 2007/0098137 A1* | 5/2007 | Joshi et al. | 378/19 |
| 2007/0116344 A1* | 5/2007 | Hsieh et al. | 382/131 |
| 2007/0121781 A1* | 5/2007 | Meirav et al. | 378/19 |
| 2007/0131858 A1* | 6/2007 | Wollenweber et al. | 250/252.1 |
| 2008/0006773 A1* | 1/2008 | Rose et al. | 250/336.1 |

OTHER PUBLICATIONS

Office Action dated Sep. 19, 2008 U.S. Appl. No. 11/560,873.
Office Action dated Mar. 20, 2009 U.S. Appl. No. 11/560,873.
NL Search Report and Opinion—Jun. 19, 2009.
State Intellectual Property Office, P.R.China, English Translation of First Office Action issued on Apr. 13, 2010, pp. 1-10.

* cited by examiner

ELECTRICAL INTERFACE FOR A SENSOR ARRAY

FIELD OF THE INVENTION

The present invention is generally related to an electrical interface for a sensor array, and, more particularly, to an integrated circuit (IC) based electrical interface between the sensor array and a data acquisition system (DAS), as may be used in a computed tomography (CT) system.

BACKGROUND OF THE INVENTION

Electronic devices, such as sensors, transceivers, transmitters, receivers, antennas, etc., may be configured in arrays to transmit or receive data in a two dimensional format or to effect a desired resolution for a given area. For example, one known sensor used in a computed tomography (CT) system includes a photodiode including an array of photosensitive pixels coupled to a scintillating medium, which can also be configured as an array of scintillator cells. When subjected to x-ray energy, the scintillator generates optical photons which in turn excite the underlying photosensitive pixels within the photodiode thereby producing an analog electrical signal corresponding to an incident photon flux.

One exemplary CT detector array is known to be configured with a plurality of sensor elements, where, as described above, each sensor element in the CT detector array in turn comprises an x-ray scintillator deposited on a pixel array of photosensitive light sensors. Thus, even a single sensor element may be referred to herein as "sensor arrays." A data acquisition system (DAS) may acquire the analog signals from the sensors and convert these signals to digital signals for subsequent processing.

Interface packages traditionally utilized between the sensor arrays and the DAS have not enabled achieving optimal signal integrity for the analog signals. For example, this may entail simultaneously reducing the number and/or distance of the interconnect paths between the photodiode array and the DAS, and reducing crosstalk between the analog inputs and the digital signals and power connections. One issue that could arise is that if one locates the DAS adjacent to the photodiode array, this may necessitate providing a radiation shield for protecting one or more application specific integrated circuits (ASICS) that may be constructed in the DAS. Moreover, depending on the needs of a given application, it would also be desirable to reduce other effects, such as electromagnetic interference (EMI) and/or electromagnetic compatibility (EMC).

Accordingly, it is desirable to provide an interface architecture that cost-effectively addresses the issues noted above. For example, this would enable a CT detector architecture having superior performance in various aspects, such as reducing level of crosstalk and EMI, providing an efficient thermal coupling between the DAS and the sensor array, and a concomitant increased reliability.

BRIEF DESCRIPTION OF THE DRAWINGS

These and other advantages of the invention will be more apparent from the following description in view of the drawings that show.

DETAILED DESCRIPTION OF THE INVENTION

Figure 1:
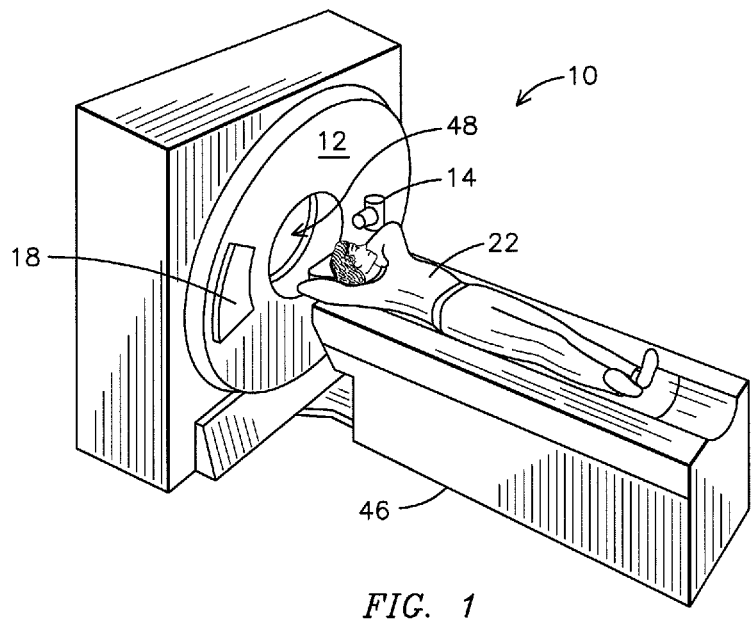
FIG. 1 is an isometric view of an exemplary CT imaging system, as may use a CT sensor array for medical imaging.

As used herein, a "sensor array" refers to a component comprising one or more individual sensors. In many configurations, a sensor array may itself comprise a component having, for example, a two-dimensional array of sensors, and a plurality of sensor arrays may be assembled into a larger assembly referred to as a "detector array." A "sensor array" may comprise an M×N array of sensors; wherein both M and N are integer numbers equal to or greater than one. Thus, the scope of the term "sensor array" is not intended to exclude devices having only one sensor.

By way of illustration, the description below refers to a CT imaging system. It is noted, however, that aspects of the present invention may be advantageously used in various other applications, which are limited neither to medical imaging applications nor to a CT modality. Examples of other modalities may be magnetic resonance, ultrasound, positron emission tomography, and a multi-energy computed tomography. Examples of other applications may be equipment inspections and diagnostics as may be performed in an industrial setting or security inspections as may be performed in a transportation setting, such as a baggage scanning for an airport or container inspection in a port, etc.

In some CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each sensor of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of aspects of the present invention in which data representing an image is generated but a viewable image is not. However, many embodiments generate (or are configured to generate) at least one viewable image.

Figure 2:
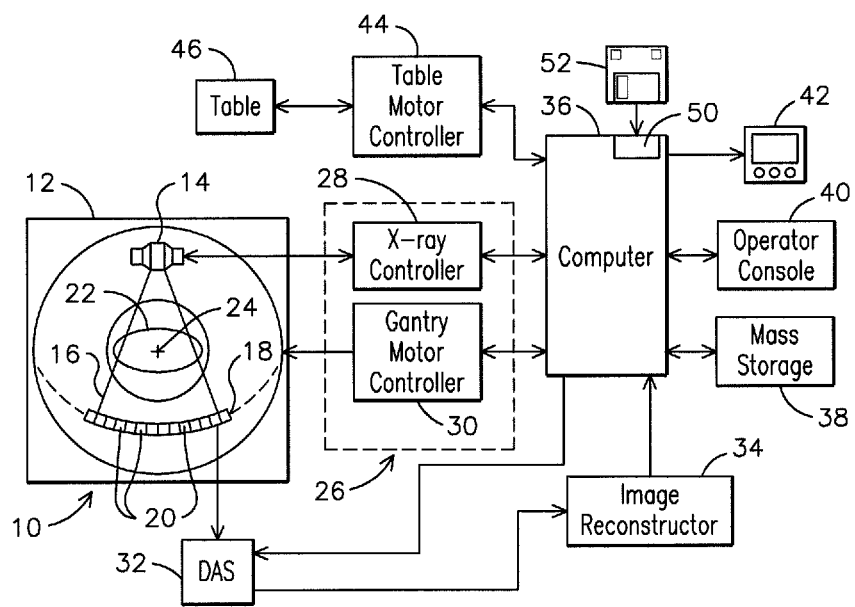
FIG. 2 is a block diagram representation of a CT imaging system as seen in FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has an x-ray tube 14 (also called x-ray source 14 herein) that projects a beam of x-rays 16 toward a detector array 18 on the opposite side of gantry 12. Detector array 18 is formed by a plurality of detector rows (not shown) including a plurality of sensors 20 which together sense the projected x-rays that pass through an object, such as a medical patient 22 between array 18 and source 14. Each sensor 20 produces an electrical signal that represents the intensity of an impinging x-ray beam and hence can be used to estimate the attenuation of the beam as it passes through object or patient 22.

During a scan to acquire x-ray projection data, gantry 12 and the components mounted therein rotate about a center of rotation 24. FIG. 2 shows only a single row of sensors 20 (i.e., a detector row). However, multi-slice detector array 18 includes a plurality of parallel detector rows of sensors 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 may be connected (as described below in greater detail using an electrical interface embodying aspects of the present invention) to receive analog signals from sensors 20 and convert the analog signals to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

In one embodiment, computer 36 includes a device 50, for example, a floppy disk drive, CD-ROM drive, DVD drive, magnetic optical disk (MOD) device, or any other digital device including a network connecting device such as an Ethernet device for reading instructions and/or data from a computer-readable medium 52, such as a floppy disk, a CD-ROM, a DVD or another digital source such as a network or the Internet, as well as yet to be developed digital means. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein. Although the specific embodiment mentioned above refers to a third generation CT system, the methods described herein equally apply to fourth generation CT systems (stationary detector—rotating x-ray source) and fifth generation CT systems (stationary detector and x-ray source).

For readers desirous of general background information regarding an exemplary sensor array, such as a tileable sensor array, that may benefit from aspects of the present invention, reference is made to U.S. Pat. No. 6,990,176, which is assigned in common to the same assignee of the present invention and is herein incorporated by reference. The sensor array described in the foregoing patent may be used with a system, such as a computed tomography imaging system, a magnetic resonance imaging system, a Positron Emission Tomography (PET) system, and a multi-energy computed tomography imaging system.

A transducer broadly refers to a device for converting a signal in a given physical form, such as radiation, sound, temperature, pressure, light or other physical form to (or from) an electrical signal. In an example embodiment, a sensor array may include a plurality of transducers configured to receive an input signal in a given physical form and transmit a desired electrical output signal. For example, a transducer array may include a plurality of sensor devices, such as a photodiode, a back-illuminated photodiode, a sonic sensor, i.e. a sensor configured to detect sounds, a temperature sensor, and an electromagnetic radiation sensor. For purposes of the present invention, the basic concept being that a sensor array regardless of its specific implementation may generally employ an electrical interface to supply the signals sensed by the array.

The inventors of the present invention have innovatively recognized a chip scale interface architecture that allows segregating (e.g., in an integrated circuit package) signals having a given electrical characteristic (e.g., relatively sensitive analog signals) from signals having different electrical characteristics with respect to the given electrical characteristic (e.g., digital and/or power signals). One example embodiment may be used in a data acquisition system that provides a desired signal conditioning (e.g., analog-to-digital conversion) to the sensitive analog signals from a CT detector array. In one example embodiment, the interface architecture may feature appropriately disposed vias (i.e., vertical interconnects) within the package that allow segregating the analog sensor interconnections from the digital and power interconnections. For example, the analog interconnections may be made at a first region of the package (e.g., a top face of the package), and the digital signals and power interconnections may be made at a second region spaced apart from the first region (e.g., a bottom face of the package). It is contemplated that the top face of the package need not be limited to analog signals from the sensor array since, for example, one could provide at least one or more I/Os 111 (FIG. 4) on this face that may be used for IC testing, but not be used in the final application. For example, this may reduce the number of I/Os on the mostly digital I/O side of the package.

Figure 3:
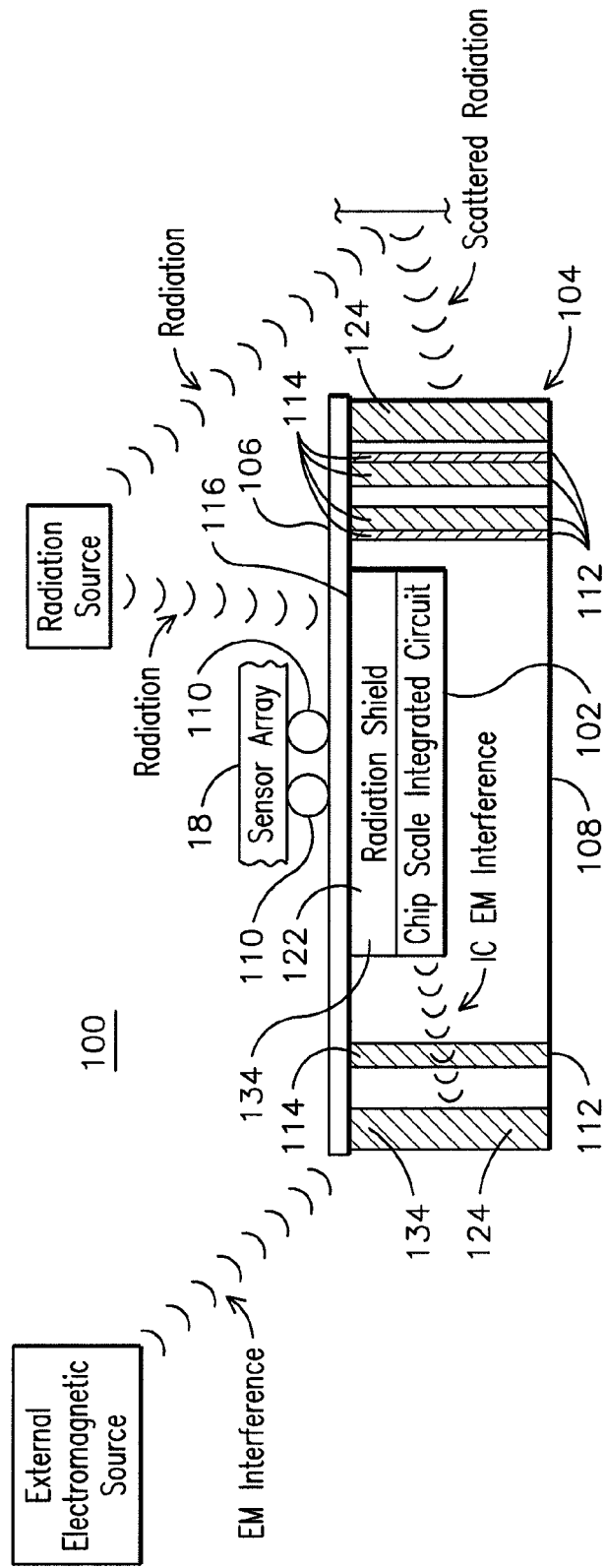
FIG. 3 is a cross sectional view of an electrical interface embodying aspects of the present invention, as such interface may be assembled in an integrated circuit package for electrically interconnecting with a sensor array.

FIG. 3 is a cross sectional view of an electrical interface circuit 100 for a sensor array 18. The interface circuit may be fabricated using standard integrated circuit manufacturing technology. Accordingly, for the sake of avoiding unnecessary details the reader will be spared from minutia that should be readily understood by one skilled in the art. For readers desirous of general background information regarding various processes and materials used in IC fabrication, reference is made to textbook titled "Silicon Processing For The VLSI Era, Vol. 1—Process Technology, $2^{nd}$ Edition by S. Wolf and R. N. Tauber, published and copyrighted by Lattice Press, which textbook is herein incorporated by reference.

The interface circuit includes a package 104 that defines a first region 106 (e.g., a top face) and a second region 108 (e.g., a bottom face). The first region of the package includes a plurality of interfaces (e.g., top interfaces 110) for interconnecting an integrated circuit 102, such as an ASIC configured to provide suitable analog-to-digital conversion, to a plurality of signals having a first electrical characteristic (e.g., relatively sensitive analog signals from sensor array 18). The second region of the package comprises a plurality of bottom interfaces 112 for interconnecting to the integrated circuit a plurality of signals having at least one electrical characteristic different than the first characteristic (e.g., digital signals and power signals).

Figure 5:
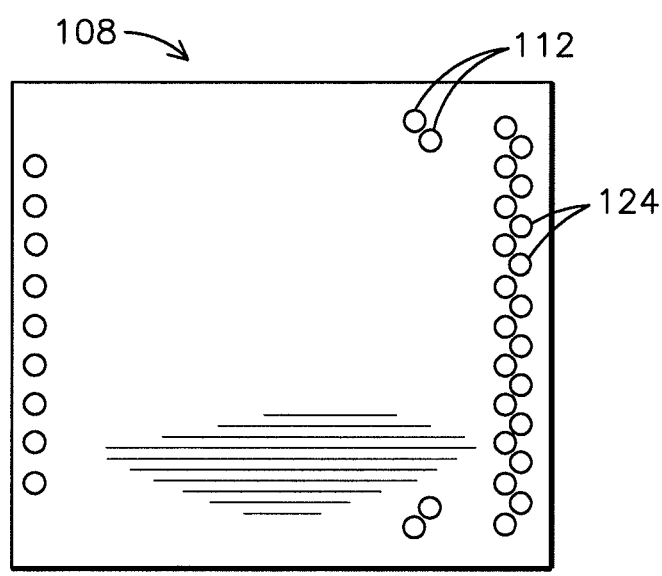
FIG. 5 is a view of the face of the interface package as may be configured for interconnecting to digital and power signals, thereby segregating such signals from the sensor array signals received at the top face of the package.

An example embodiment of the second region and bottom interfaces 112 may be better appreciated in FIG. 5, which illustrates a bottom view of the interface package. A plurality of electrically conductive vias 114 may be disposed to provide a plurality of electrical paths, such as generally vertical paths disposed between the second region and the first region of the interface package and may be interconnected to one or more routing layers 116 for electrical routing the digital and power signals received at the bottom face to the ASIC.

Figure 4:
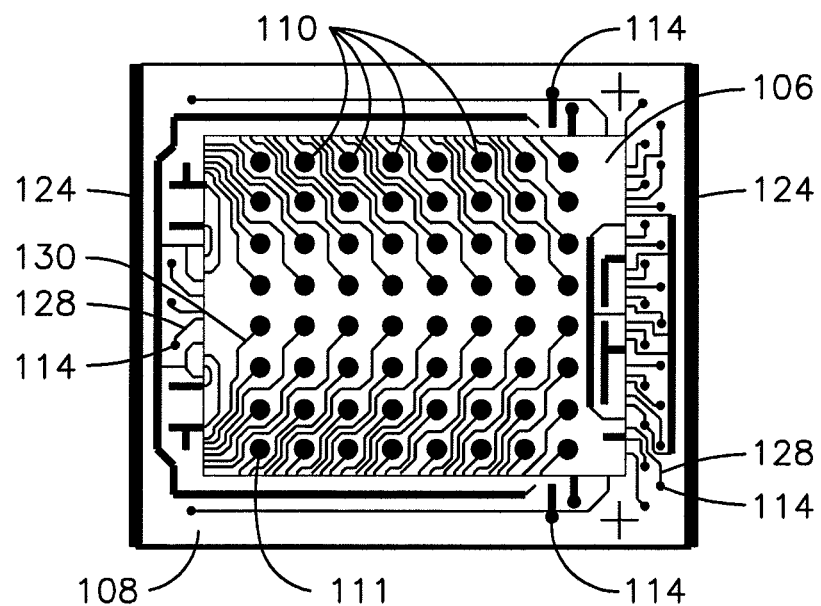
FIG. 4 is a view of the top face of the interface package showing an example array of interface pads arranged to match an array of corresponding sensor interface pads.

FIG. 4 is a top view of the interface package that shows, at first region 106, a first plurality of lines 130 connected to top interfaces 110 for electrically coupling the plurality of analog signals from sensor array 18 (FIG. 3) to data acquisition system (DAS) 32 (FIG. 1), which includes at least one integrated circuit 102 (FIG. 3). FIG. 4 further shows a second plurality of lines 128 for interconnecting to the integrated circuit 102 the plurality of digital or power signals by way of vias 114 connected to bottom interfaces 112 at second region 108. Accordingly, an example path for an analog signal would be from sensor array 18 (FIG. 3) to top interface 110 to line 130 to integrated circuit 102 (FIG. 3). Conversely, an example path for a digital signal would be from integrated circuit 102 to line 128 to via 114 to bottom interface 112. It would be readily appreciated that, in a reverse direction, this could be a path for a power signal. That is, from bottom interface 112 to via 114 to line 128 to integrated circuit 102.

In one example embodiment better appreciated in FIG. 4, the top face of the interface package comprises an array of interface pads 110 arranged to match an array of corresponding sensor array interface pads (not shown). It is envisioned that this arrangement may be particularly advantageous since it essentially allows a direct connection (i.e., without interconnecting leads) between the sensor array and the DAS package, as schematically represented in FIG. 3. In one example embodiment, such direct connections may be made using any of various means for electrically connecting two elements, such as solder, an anisotropic conductive film (ACF) or paste (ACP), an ultrasonic bonding, a thermosonic bonding, and a thermocompression bonding.

In one example embodiment, such as in CT application where the ASIC may be subjected to X-ray radiation, it is contemplated that one may optionally provide a radiation shield 122 (FIG. 3), such as a slug made of tungsten or any other suitable metal or alloy, positioned to block X-rays from a radiation source (as shown in FIG. 3) that otherwise could pass through the top face of the package onto the ASIC in the package. It is contemplated that a flip-chip CSP (Chip Scale Package) may be preferred in an example embodiment without a top radiation shield 122, and a wirebond CSP may be used when top radiation shield 122 is utilized.

In another example embodiment, one may provide one or more lateral shields 124 (e.g., tungsten slugs or any other suitable metal or alloy) that may block scattered X-ray radiation, as shown in FIG. 3. It will be appreciated that the lateral shields may also function as an EMI shield. Essentially, the combination of top shield 122 and lateral shield/s 124 may be configured to function as a Faraday cage 134 in environments subject to relatively large electromagnetic fields from an electromagnetic source (as shown in FIG. 3), e.g., a magnetic resonance application. The lateral shield may take various forms, such as (a singular or segmented ring) that extends along the periphery of the package, or may take the form of a nested shield or a honeycomb-like structure. The ASIC, shields, and interconnecting structures may be encapsulated in the IC package by a suitable encapsulant.

It is contemplated that the described electrical interface architecture will enable an assembly that in one example application, such as in a multi-slice CT system, provides the following exemplary advantages: reduction of unwanted parasitics (e.g., an undesired signal current, capacitance, inductance or other parameter in an electronic circuit and/or interface) thereby increasing sensor array signal integrity, relatively uncomplicated manufacturing and serviceability, reduced cost, improved reliability through reduction of number and/or length of interconnects, reduction of shear forces on the electronics, increased available cooling volume in the CT detector, and available volume for providing temperature tracking and control of the detector. As noted above, an electrical interface architecture embodying aspects of the present invention can be used in sensor arrays based on diverse sensing modalities.

While the preferred embodiments of the present invention have been shown and described herein, it will be obvious that such embodiments are provided by way of example only. Numerous variations, changes and substitutions will occur to those of skill in the art without departing from the invention herein. Accordingly, it is intended that the invention be limited only by the spirit and scope of the appended claims.

The invention claimed is:

1. A system comprising:
an array of sensors based on a given sensing modality;
an interface for electrically coupling a plurality of analog signals from the array of sensors to a data acquisition system comprising at least one integrated circuit for providing a desired signal conditioning to the analog signals; and
a chip scale integrated circuit package for the interface comprising at least a first region and a second region, the first region being spaced apart and opposite to the second region of the package, wherein the first region of the package comprises a plurality of interfaces and a first plurality of lines for interconnecting to the integrated circuit the analog signals from the sensor array, and wherein the second region of the package comprises a plurality of interfaces for interconnecting to electrically conductive vias disposed between the second region and the first region of the package, and, through a second plurality of lines, for interconnecting to the integrated circuit and wherein the first and second plurality of lines are arranged in the integrated circuit package to segregate the analog signals, a plurality of digital or power signals carried by the second plurality of lines, thereby segregating within the integrated circuit package the analog signals from the plurality of digital or power signals.

2. The system of claim 1 further comprising a routing layer electrically interconnected to a respective via for routing to the integrated circuit a signal received at the second region of the package.

3. The system of claim 1 wherein the first region of the package further comprises at least one interface for interconnecting to a respective test signal.

4. The system of claim 1 wherein the sensing modality for the sensor array is selected from the group consisting of magnetic resonance, ultrasound, positron emission tomography, and computed tomography.

5. The system of claim 1 further comprising a shield disposed to block radiation directed from a radiation source, which otherwise would pass through the first region and into the integrated circuit.

6. The system of claim 1 further comprising at least one lateral shield interposed between the first and second regions of the package to block radiation scattered from the radiation source into the integrated circuit.

7. The system of claim 1 further comprising an upper shield to block entry of radiation directed from a radiation source through the first region and into the integrated circuit, and further comprising at least one lateral shield interposed between the first and second regions of the package to block entry of radiation scattered from the radiation source into the integrated circuit.

8. The system of claim 1 further comprising an upper shield adjacent to at least a portion of the first region and further comprising at least one lateral shield interposed between the first and second regions of the package, the combination of said upper shield and lateral shield constituting a Faraday cage to reduce electromagnetic interference from at least one of the following: from an external electromagnetic source into the integrated circuit and from the integrated circuit to neighboring electrical devices.

9. An interface circuit for a sensor array, the interface circuit comprising:
a chip scale integrated circuit package comprising a first region and a second region, the first region being spaced apart and opposite to the second region of the package, wherein the first region of the package comprises a plurality of interfaces and a first plurality of lines for interconnecting to an integrated circuit in the package a plurality of analog signals from the sensor array, and wherein the second region of the package comprises a plurality of interfaces for interconnecting to electrically conductive vias disposed between the second region and the first region of the package and, through a second plurality of lines, for interconnecting to the integrated circuit, and wherein the first and second plurality of lines are arranged in the integrated circuit package to segregate from the analog signals, a plurality of digital or power carried by the second plurality of lines, thereby segregating within the integrated circuit package the analog signals from the plurality of digital or power signals.

10. The interface circuit of claim 9 wherein the first region of the package further comprises at least one interface for interconnecting to a respective test signal.

11. The interface circuit of claim 9 further comprising a routing layer electrically interconnected to a respective via for routing to the integrated circuit a signal received at the second region of the package.

12. The interface circuit of claim 9 wherein a sensing modality for the sensor array is selected from the group consisting of magnetic resonance, ultrasound, positron emission tomography, and computed tomography.

13. The interface circuit of claim 9 further comprising a shield disposed to block radiation directed from a radiation source, which otherwise would pass through the first region and into the integrated circuit.

14. The interface circuit of claim 9 further comprising at least one lateral shield interposed between the first and second regions of the package to block radiation scattered from the radiation source into the integrated circuit.

15. The interface circuit of claim 9 further comprising an upper shield to block entry of radiation directed from a radiation source through the first region and into the integrated circuit, and further comprising at least one lateral shield interposed between the first and second regions of the package to block entry of radiation scattered from the radiation source into the integrated circuit.

16. The interface circuit of claim 9 further comprising an upper shield adjacent to at least a portion of the first region and further comprising at least one lateral shield interposed between the first and second regions of the package, the combination of said upper shield and lateral shield constituting a Faraday cage to reduce electromagnetic interference from at least one of the following: from an external electromagnetic source into the integrated circuit and from the integrated circuit to neighboring electrical devices.

* * * * *